United States Patent [19]

Lauer et al.

[11] 3,997,786
[45] Dec. 14, 1976

[54] SYSTEM FOR SPECTROSCOPIC ANALYSIS OF A CHEMICAL STREAM

[75] Inventors: James L. Lauer, Penn Wynne; Melvin E. Peterkin, Brookhaven, both of Pa.

[73] Assignee: Sun Oil Company of Pennsylvania, Philadelphia, Pa.

[22] Filed: Aug. 25, 1975

[21] Appl. No.: 607,657

[52] U.S. Cl. ............................................. 250/343
[51] Int. Cl.² ...................................... G01N 21/26
[58] Field of Search .................. 250/343, 353, 505

[56] References Cited

UNITED STATES PATENTS

| | | | |
|---|---|---|---|
| 3,319,071 | 5/1967 | Werth et al. | 250/343 X |
| 3,370,502 | 2/1968 | Wilks, Jr. | 250/343 X |
| 3,394,253 | 7/1968 | Harrick et al. | 250/353 |
| 3,490,847 | 1/1970 | Berz et al. | 250/505 X |
| 3,920,993 | 11/1975 | Cederstrand et al. | 250/343 |

Primary Examiner—Davis L. Willis
Attorney, Agent, or Firm—J. Edward Hess; Donald R. Johnson; William C. Roch

[57] ABSTRACT

A system for performing an on-stream analysis of the chemical composition of a refinery stream. A U-shaped radiation waveguide having a plurality of small apertures therein is inserted into the refinery stream. Far infra-red radiation is introduced into one end of the waveguide. The apertures in the waveguide allow the chemical stream to circulate freely within it, resulting in selective absorption of the radiation traveling through the waveguide which is dependent upon the chemical composition of the stream. A detector detects radiation exiting from the waveguide, and produces a graph of radiation intensity versus wavelength for the far infra-red portion of the spectrum. A spectroscopic analysis of the graph indicates the chemical composition of the stream.

7 Claims, 1 Drawing Figure

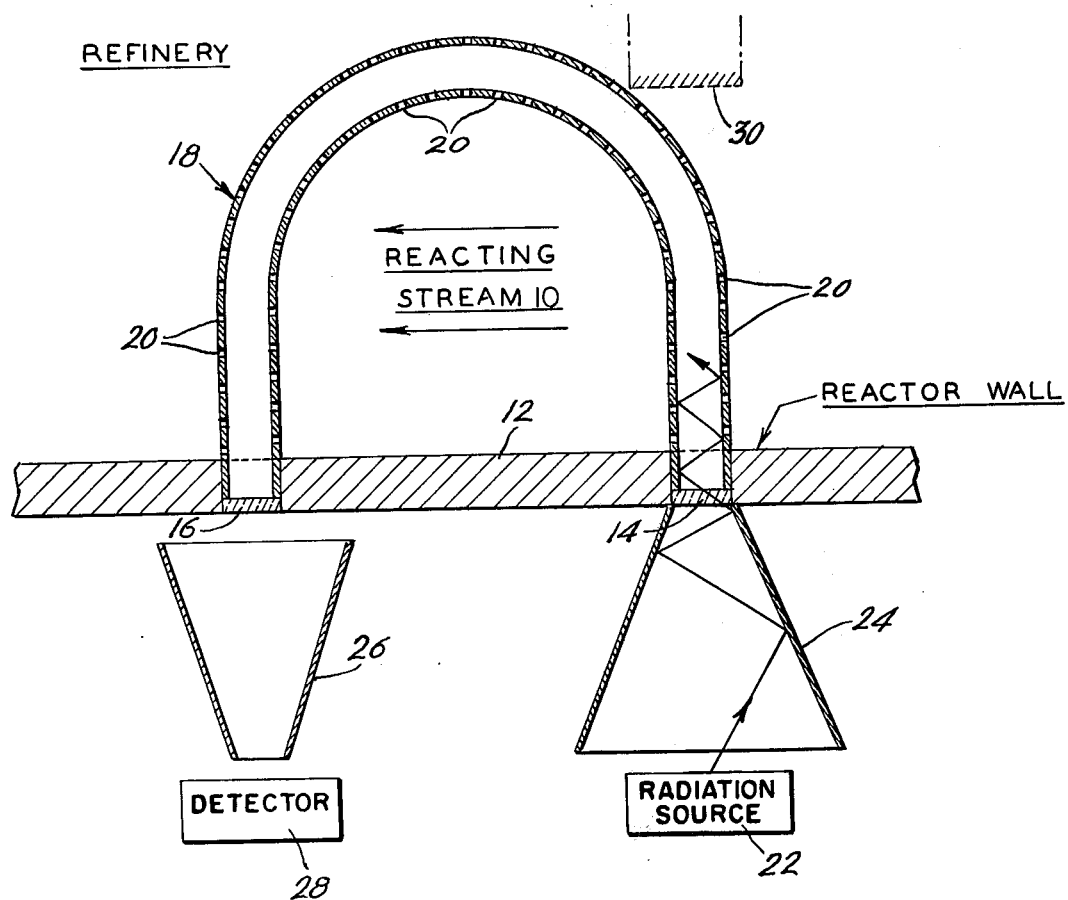

SYSTEM FOR SPECTROSCOPIC ANALYSIS OF A CHEMICAL STREAM

BACKGROUND OF THE INVENTION

The present invention relates generally to the field of spectroscopy, and more particularly relates to an application of the principles of spectroscopy to an on-stream analysis of a chemical stream in a refinery. More particularly, the present invention relates to the application of spectroscopic principles to the analysis of a stream containing alkylates and aromatics and derived from the refining of lubricating oils.

SUMMARY OF THE INVENTION

In accordance with a preferred embodiment, a system is disclosed for obtaining an on-stream spectroscopic analysis of a chemical stream. A radiation waveguide having a plurality of apertures is immersed in the chemical stream, and the apertures allow the stream to flow freely through the waveguide. Radiation is introduced into one end of the waveguide and travels through the chemicals in the waveguide to a detector at the other end of the waveguide. The nature of the chemical composition of the stream may then be ascertained by the radiation absorbed by the chemical stream.

BRIEF DESCRIPTION OF THE DRAWING

The drawing illustrates one embodiment of the present invention.

DETAILED DESCRIPTION OF AN EMBODIMENT

Referring to the FIGURE, there is illustrated a reacting stream 10 which in the disclosed embodiment is a gaseous stream of alkylates and aromatics in a refinery for the production of lubricating oils. The reacting stream flows within a conduit having a wall 12, shown in cross section. In accordance with the teachings of this invention, two windows 14 and 16 are placed in the wall, and a U-shaped radiation waveguide 18 extends into the reacting stream and between the two windows. The radiation waveguide has a plurality of small apertures 20 in its wall to allow the reacting stream to flow freely through it. The entire waveguide is submerged in the reactor stream, and accordingly during operation there should be little difficulty from temperature gradients. A source of far infra-red radiation 22, such as a mercury arc lamp, is utilized to supply radiation for the waveguide. Aromatics are particularly sensitive to radiation in the far infra-red portion of the spectrum, and also the far infra-red spectral region has only one or two absorption bands within a fairly wide range of the spectrum. This makes analysis of the resulting spectrogram much simpler as a small number of absorption bands results in less interference and an easier and more definite analysis. A conical waveguide 24 is utilized to increase the intensity of the radiation before it enters the waveguide 18. Radiation which has traveled through the length of the waveguide 18 exits through window 16 into a second cone shaped waveguide 26 which concentrates the radiation onto a detector 28.

The length of the waveguide 18 would depend upon the type and density of material within the chemical stream, and would typically be several feet. The apertures 20 would be rather small such that only a small portion of the radiation would be lost through them, but would be large enough to allow the chemical stream to flow freely through the waveguide. Since the U-shaped is substantially constant in cross sectional area, its design is relatively simple, and may be simply a reflecting tube. The conical shaped waveguides 24 and 26 are designed as surfaces of revolution approximating cones.

The detector 28 may be any one of several different types of available detectors which are capable of detecting radiation at different wavelengths to enable a determination of the far infra-red absorption characteristics of the chemical stream. The detector may be spectrophotometer, such as a General Electric recording spectrophotometer, or it may be a solid state detector specifically designed for far infra-red radiation, such as an indium antimonide detector available from Texas Instruments, or it might be a Golay cell, or it might be a pyroelectric detector such as lithium lanthanide detector. Commercially available detectors for the far infra-red portion of the spectrum have relatively fast response times, and accordingly the present invention is useful for detecting real-time reactor changes.

The FIGURE also illustrates in dotted lines some details of another embodiment of the present invention. In that embodiment, a reflecting element 30 would be positioned in the chemical stream to redirect the radiation back through the same window 14 or through another window, to a detection system. Reflecting element 30 may preferably be formed of an inert and highly reflective material such as gold.

Although the drawing illustrates at least one embodiment of the present invention, other embodiments might be designed with different optical figurations. For instance, the waveguide 18 might be simply a straight tube with a retro-reflector mounted at its end, and with the radiation source and detector operating through different portions of one window. Also, if the diameter of the conduit for the chemical stream were small, the radiation might be simply directed across the stream to the other side of the conduit, with the radiation source on one side and the detector on the opposite side of the conduit.

Although at least one embodiment of the present invention has been described, the teachings of this invention will suggest many other embodiments to those skilled in the art.

The invention claimed is:
1. A system for performing an on-stream analysis of the composition of a chemical stream and comprising:
    a. a retainer wall means for containing a chemical stream on which an analysis is desired;
    b. at least one window means mounted in said retainer wall means for allowing radiation to be transmitted through said retainer wall into the chemical stream;
    c. radiation waveguide means supported adjacent to said window and extending into the flow of the chemical stream, said radiation waveguide means having apertures therein for allowing the chemical stream to continuously flow through it;
    d. means for introducing a radiation beam through said at least one window means and into said radiation waveguide means whereby the radiation will be transmitted through the chemical stream within said radiation waveguide means, and depending upon the nature of the chemical stream, given wavelengths of the radiation beam will be selectively attenuated; and e. means, positioned adjacent to said at least one window means, for detecting radiation which has traveled through the chemical stream, whereby the nature of the chemical stream may be ascertained by the radiation absorbed by the chemical stream.

2. A system as set forth in claim 1 wherein said radiation waveguide means includes a U-shaped radiation waveguide extending into the flow of the chemical stream, said at least one window means includes first and second windows mounted in said retainer wall, one window for each leg of said U-shaped radiation waveguide, said means for introducing a radiation beam introduces radiation through said first window into said U-shaped radiation waveguide, and said means for detecting radiation detects radiation which has traveled through said U-shaped radiation waveguide and said second window.

3. A system as set forth in claim 2 wherein said means for introducing a radiation beam includes means for introducing a far infra-red radiation beam.

4. A system as set forth in claim 3 wherein said detecting means includes means for detecting and displaying radiation in the far infra-red portion of the spectrum.

5. A system as set forth in claim 4 wherein the chemical stream being analyzed is a chemical stream involved in the refining of lubricating oils and contains alkylates and aromatics.

6. A system as set forth in claim 5 wherein said introducing means includes a conical shaped waveguide means for intensifying the far infra-red radiation introduced into said U-shaped waveguide.

7. A system as set forth in claim 6 wherein said detecting means includes a conical shaped waveguide means for focusing far infra-red radiation on a detector.

* * * * *